US00PP25918P3

(12) United States Plant Patent
Keogh

(10) Patent No.: US PP25,918 P3
(45) Date of Patent: Sep. 22, 2015

(54) **VARIETY OF *TIBOUCHINA* NAMED 'COOL BABY'**

(50) Latin Name: *Tibouchina×hybrida*
Varietal Denomination: Cool Baby

(71) Applicant: Terry Keogh, Victoria Point (AU)

(72) Inventor: Terry Keogh, Victoria Point (AU)

( * ) Notice: Subject to any disclaimer, the term of this patent is extended or adjusted under 35 U.S.C. 154(b) by 178 days.

(21) Appl. No.: 13/815,690

(22) Filed: Mar. 14, 2013

(65) Prior Publication Data

US 2014/0283246 P1 Sep. 18, 2014

(51) Int. Cl.
*A01H 5/02* (2006.01)

(52) U.S. Cl.
USPC ..... Plt./226
CPC ..... *A01H 5/02* (2013.01)

(58) Field of Classification Search
USPC ..... Plt./226, 263.1
See application file for complete search history.

*Primary Examiner* — Anne Grunberg
(74) *Attorney, Agent, or Firm* — The Webb Law Firm

(57) ABSTRACT

'Cool Baby' is a new variety of *Tibouchina* plant that is suitable for planting in gardens, containers, and in landscaping having tolerance to low temperatures and white flowers with purple margins.

2 Drawing Sheets

Botanical classification: *Tibouchina×hybrida.*
Varietal denomination: 'COOL BABY'.

BACKGROUND OF THE NEW PLANT

The present invention comprises a new and distinct cultivar of *Tibouchina* plant, botanically known as *Tibouchina×hybrida* and hereinafter referred to by the cultivar name 'Cool Baby'.

The new and ornamental variety was selected by the breeder as a result of an ongoing breeding program that has been conducted by the inventor for more than thirty years at the inventor's nursery in Victoria Point, Queensland, Australia. The purpose of the breeding program is to produce novel varieties of *Tibouchina* in varying plant sizes, flower colors, and which are well-suited to a range of climate zones. 'Cool Baby' is a hybrid plant derived from the deliberate controlled cross-pollination of the unpatented female parent, an individual plant of *Tibouchina organensis*, named 'Totally Moonstruck', and the unpatented male parent, an individual plant of *Tibouchina mutabilis* named 'Jazzie'. The inventor emasculated flowers of the female parent and applied pollen that was freshly collected from the male parent in 2003. The parent plants were isolated to prevent open pollination. In 2007, the inventor selected 'Cool Baby' as a seedling that had been raised from the cross-pollination described herein. Selection was based on the criteria of habit, flower color, plant dimensions, and cold temperature tolerance. The plant was then propagated in 2008 via vegetative cuttings to produce a new generation for final evaluation.

Further, asexual reproductions of 'Cool Baby' in Victoria Point, Queensland, Australia has demonstrated that the combination of characteristics as herein disclosed for the new cultivar are retained and reproduced true to type through more than six successive generations of asexual reproduction.

The color references made herein are to The R.H.S. Colour Chart of The Royal Horticulture Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'Cool Baby' which, in combination, distinguish this *Tibouchina* plant as a new and distinct cultivar:

1. Very compact size and with rounded plant growth (dwarf form);
2. Abundant, mid-sized white flowers with a purple margin;
3. Slow to moderate vigor;
4. Very dense habit;
5. Low temperature tolerance; and
6. Woody, long-lived shrub.

The new variety differs from 'Totally Moonstruck' and 'Jazzie' in its smaller, mature plant size. Further, 'Jazzie' exhibits purple flowers.

Further, the new variety exhibits a differing margin color, while 'Peace Baby' does not (U.S. plant patent application Ser. No. 13/815,677). 'Peace Baby' also has larger mature plant dimensions, a faster growth rate, and lighter green leaves than 'Cool Baby'.

BRIEF DESCRIPTION OF THE DRAWINGS

The accompanying photographic drawings illustrate the new variety, with the colors being as nearly true as is possible with color illustrations of this type.

PROPAGATION

Figure 1:
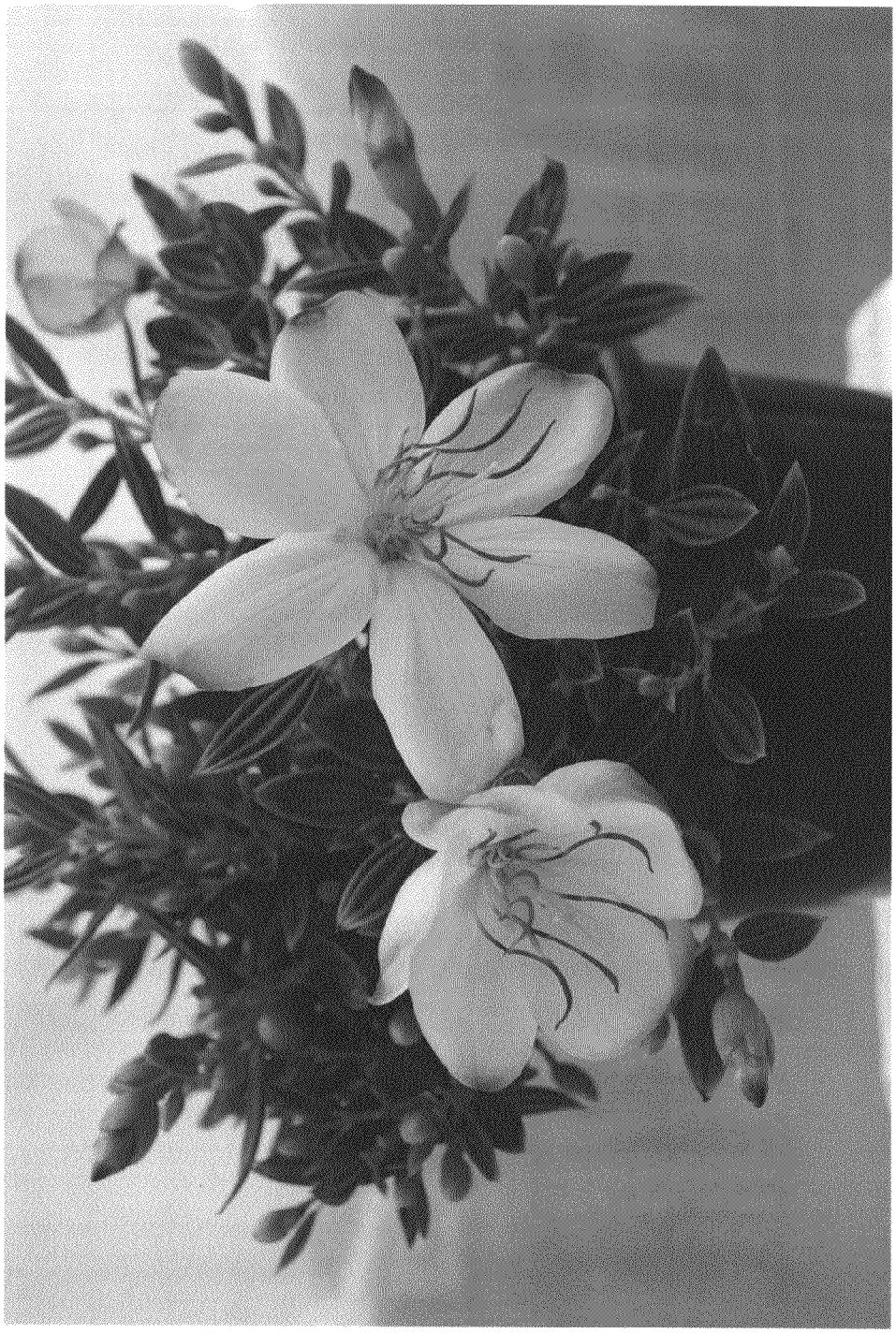
FIG. 1 is close-up photograph of a flower of the new variety.
Figure 2:
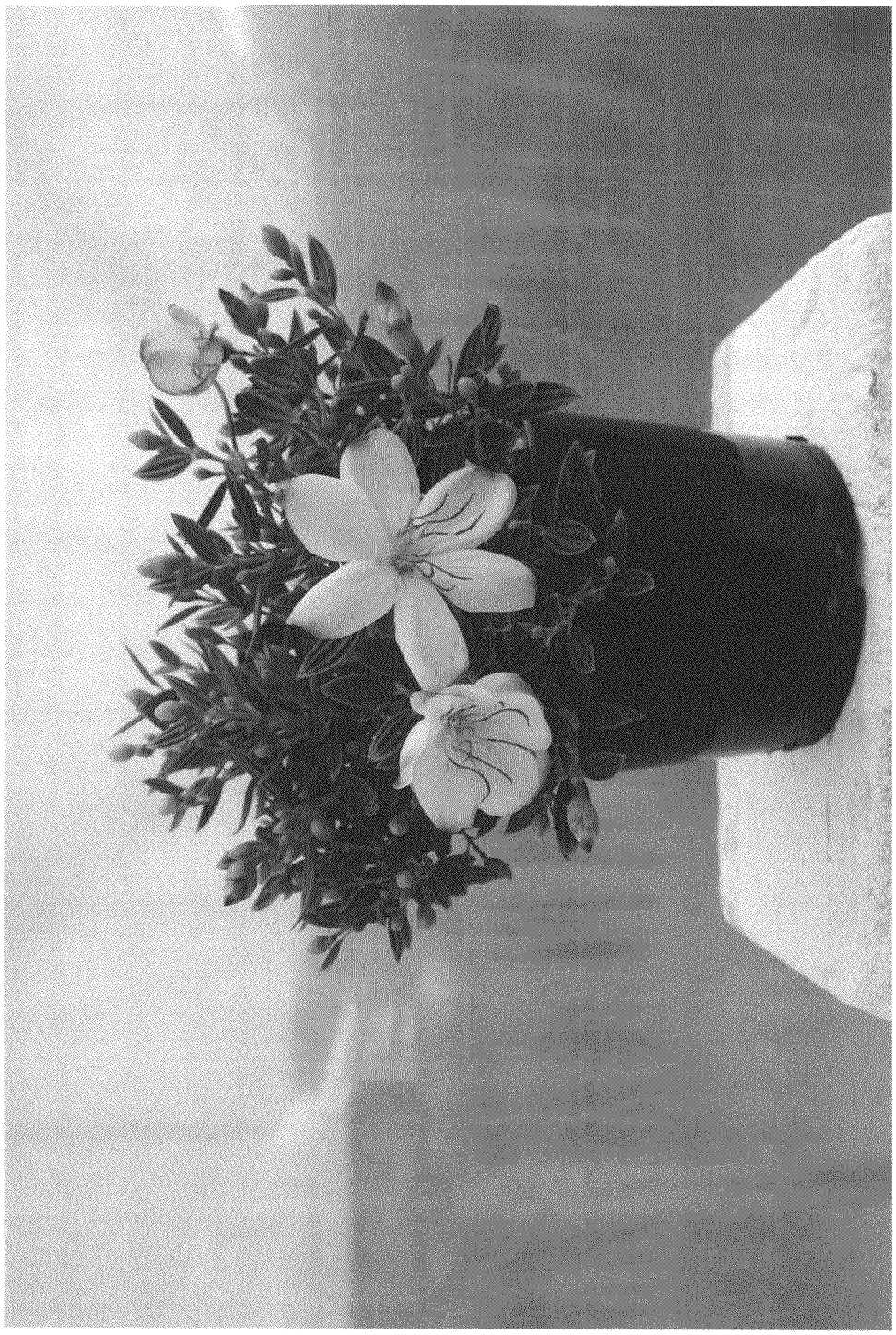
FIG. 2 is a photograph of an entire plant of the new variety

Time to initiate roots: About 18-25 days at approximately 21° C.

Time to produce a rooted cutting: About 30-40 days at 21° C.

PLANT

Plant spread: Approximately 24 cm.
Plant height: 21 cm.
Growth rate: Slow to moderate.
Temperature tolerance: USDA Hardiness Zone 9.
Lateral branches: Length: Approximately 8 cm. Diameter: Approximately 0.18 cm. Quantity: About 40.
Age of plant when described: Approximately 48 weeks from a rooted cutting.
Growth habit: Dense; compact; rounded.
Height at maturity: 60 cm.
Width at maturity: 80 cm.
Stem:
*Branching habit.*—Strong, basal branching.
*Main stem diameter.*—7 cm.
*Lateral stem length* (*average*).—8 cm.
*Lateral stem width* (*average*).—0.18 cm.
*Internode length* (*range*).—0.8 cm to 2.5 cm.
*Shape.*—Square in cross section.
*Surface.*—Rough.
*Branch color.*—Juvenile: 146D. Semi-ripe: 146B. Mature: 199B.
Foliage:
*Leaf.*—Arrangement: Opposite. Division: Simple. Margin: Entire. Shape: Ovate to elliptic. Base: Cuneate. Apex: Acute. Surface (adaxial): Finely pubescent. Surface (abaxial): Finely pubescent. Texture (adaxial surface): Prominently ribbed. Texture (abaxial surface): Prominently ribbed. Attachment: Petiolate. Length (range excluding petiole): 0.9 cm to 5.8 cm. Width (range): 0.55 cm to 2.4 cm. Color (adaxial surface): Between N189A and 147A. Color (abaxial surface): 146B. Color of juvenile foliage not fully expanded: 185A and 147A.
*Foliar fragrance.*—None observed to date.
*Venation.*—Pattern: Reticulate; 3 primary parallel veins. Color (adaxial surface): 146B. Color (abaxial surface): 146C. Prominence (adaxial surface): Depressed. Vein prominence (abaxial surface): Raised.
*Petiole.*—Length (range): 0.4 cm to 1.1 cm. Diameter (average): 0.16 cm. Color: 146C. Surface: Pubescent. Shape: Cylindrical, but flattened on the adaxial surface.
Flower:
*Shape.*—Rotate.
*Diameter.*—9.3 cm.
*Aspect.*—Facing upward and outward.
*Inflorescence type.*—Solitary.
*Persistent or self-cleaning.*—Self-cleaning.
*Blooming period.*—Summer through fall; can bloom sporadically during other times.
*Inflorescence fragrance.*—None observed to date.
*Petals.*—Number: Usually 5 in number (occasionally 6). Central color (both surfaces): 157B. Margin color (both surfaces): 77A. Central color as senesces: 76B and 76C. Length: 4.3 cm. Width: 3.4 cm. Margin: Entire. Apex: Obtuse to flattened. Base: Broadly attenuate. Shape: Irregularly obovate. Surface (abaxial and adaxial): Glabrous. Fused or unfused: Unfused.
*Buds.*—Shape: Elliptic. Color: 144C. Surface: Pubescent. Apex: Acute. Length (at first sign of petal emergence): 2 cm. Diameter: 1.05 cm.
*Calyx.*—Shape: Cupule. Color: 144C.
*Sepals.*—Quantity: 5 in number. Width : 0.56 cm. Length: 1.1 cm. Surface (adaxial): Smooth. Surface (abaxial): Pubescent. Color (adaxial surface): 144C. Color (abaxial surface): 144B. Margin: Entire. Apex: Obtuse. Base: Truncate. Fused or unfused: Unfused.
*Peduncle.*—Dimensions: 0.5 cm in length and 3 mm in diameter. Shape: Cylindrical. Color: 146D. Surface: Pubescent.
Reproductive organs:
*Stamens.*—Number: Usually 10 in number (5 long and 5 short). Color: 84B. Length: 5 longest approximately 3.4 cm; 5 shortest approximately 2.3 cm.
*Anthers.*—Color: Ranges between 79A and N81B. Shape: Sickle. Length: 5 longest approximately 1.4 cm; 5 shortest approximately 1.0 cm.
*Pollen.*—None observed.
*Pistil.*—Number: 1. Shape: Columnar. Color: 145A and 75C. Length: 2.6 cm.
*Stigma.*—Shape: Flattened. Color: 145A.
*Ovary.*—Color: N44A. Length: 1 cm. Width: 0.56 cm. Shape: Cupule. Surface: Pubescent and ribbed. Position: Inferior.
*Seeds.*—No seeds have been observed to date.

I claim:

1. A new and distinct variety of *Tibouchina* plant named 'Cool Baby' as herein described and illustrated.

* * * * *